United States Patent
Nakamura (10) Patent No.: US 8,747,373 B2
(45) Date of Patent: Jun. 10, 2014

(54) GAS MIST PRESSURE BATH DEVICE

(75) Inventor: Shoichi Nakamura, Nagano (JP)

(73) Assignees: ACP Japan Co., Ltd., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 2 days.

(21) Appl. No.: 13/138,638

(22) PCT Filed: Aug. 6, 2009

(86) PCT No.: PCT/JP2009/063956
§ 371 (c)(1), (2), (4) Date: Sep. 14, 2011

(87) PCT Pub. No.: WO2011/016125
PCT Pub. Date: Feb. 10, 2011

(65) Prior Publication Data
US 2012/0004600 A1  Jan. 5, 2012

(51) Int. Cl.
*A61M 35/00* (2006.01)
*A61F 13/00* (2006.01)
*A61H 33/04* (2006.01)
*A61H 33/14* (2006.01)

(52) U.S. Cl.
CPC .......... *A61M 35/00* (2013.01); *A61H 2033/145* (2013.01); *A61F 13/00* (2013.01)
USPC ............................ 604/289; 604/303; 604/305

(58) Field of Classification Search
CPC ............... A61H 2033/145; A61H 2201/0207; A61H 2201/025; A61H 2205/06; A61H 2205/10; A61H 33/14; A61H 35/00; A61M 35/00; A61M 1/0088; A61M 1/0084; A61M 2205/3344; A61F 2013/00174; A61F 13/00; A61F 15/008
USPC .......................................... 604/289, 303, 305
See application file for complete search history.

(56) References Cited

U.S. PATENT DOCUMENTS 4,792,097 A * 12/1988 Kremer et al. ................ 239/338
5,938,693 A *  8/1999 Carminucci .................. 607/104

(Continued)

FOREIGN PATENT DOCUMENTS

JP    H07-171189    7/1995
JP    2005-205163   8/2005

(Continued)

*Primary Examiner* — Tatyana Zalukaeva
*Assistant Examiner* — Andrew J Mensh
(74) *Attorney, Agent, or Firm* — Manabu Kanesaka (57) ABSTRACT

The invention is to provide a gas mist pressure bath device, which causes to contact carbon dioxide, oxygen or a mixed gas of carbon dioxide and oxygen to the skin or mucous membrane of the head of a living body at pressure higher than a predetermined value for efficiently enabling skin-pass absorption. This device is to cause oxygen, carbon dioxide or a mixed gas of oxygen and carbon dioxide at density higher than a predetermined value to contact the skin or mucous membrane of the head of the living body, and is composed of a gas mist generation means 11 of generating and supplying a mist prepared by pulverizing and dissolving gas and liquid; a compressed air supply means 12 of supplying compressed air; and a living body mask member 13 shaped for covering the head of the living body, having a first sealed layer 14 which is connected to the gas mist generation means 11 and to the compressed air supply means 12, and having a second sealed layer 15 for sealing compressed air supplied from the compressed air supply means 12, so that the gas mist is caused to contact to the skin or mucous membrane of the head of the living body by the second sealed layer 15 at pressure higher than a predetermined value.

13 Claims, 9 Drawing Sheets

(56) References Cited

U.S. PATENT DOCUMENTS

| | | | |
|---|---|---|---|
| 5,957,162 A * | 9/1999 | Arai | 138/31 |
| 5,980,497 A * | 11/1999 | Yavitz | 604/294 |
| 6,638,270 B2 * | 10/2003 | Johnson | 604/890.1 |
| 2004/0243026 A1 * | 12/2004 | Toepfer et al. | 601/15 |
| 2008/0021373 A1 * | 1/2008 | Rosati | 604/22 |
| 2010/0179470 A1 * | 7/2010 | Nakamura | 604/23 |
| 2010/0305497 A1 * | 12/2010 | Tanaka et al. | 604/23 |

FOREIGN PATENT DOCUMENTS

| | | |
|---|---|---|
| JP | 2007-181720 | 7/2007 |
| JP | 2008-012268 | 1/2008 |
| JP | 2009-011695 | 1/2009 |
| JP | 2009-018136 | 1/2009 |
| JP | 2009018136 A * | 1/2009 |
| JP | U 3150690 | 4/2009 |
| WO | WO 2004/002393 | 1/2004 |

* cited by examiner

GAS MIST PRESSURE BATH DEVICE

RELATED APPLICATIONS

The present application is National Phase of International Application No. PCT/JP2009/063956 filed Aug. 6, 2009

TECHNICAL FIELD

The present invention relates to a gas mist pressure bath device, in which a gas mist is prepared by pulverizing and dissolving carbon dioxide, oxygen, or a mixed gas of carbon dioxide, oxygen and liquid, and the thus prepared gas mist is directly contacted to a skin or mucous membrane of a living-body for improving a blood circulation.

BACKGROUND ART

It has conventionally been known that carbon dioxide (carbonic acid anhydride: $CO_2$) has both properties of being not only soluble in water (water-soluble) but also soluble in fat (fat-soluble) and, therefore, by only contacting the skin and mucous membrane of the living-body being like mixed with water and fat, carbon dioxide penetrates under a subcutaneous layer and expands blood vessels around the parts of penetrated carbon dioxide, and it works to improve the blood circulation. Owing to this action of accelerating the blood circulation, it displays various physiological effects such as dropping of blood, pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living-body works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen, and the cell becomes unable to receive oxygen. As is seen, carbon dioxide seems to have been a waste product resulted from action of the cell, however, it plays in fact very important roles in the living-body.

Further, in recent times, oxygen of high density has also widely been known as effective in activity of metabolism, fatigue recovery or stability of blood pressure.

As a prior art for causing carbon dioxide to be absorbed into limited parts of the human living body, in particular the head (frontal region, parietal region, occipital region, temporal region, face and neck), there has been disclosed up to now, for example, a cosmetic instrument of causing hot water dissolved with carbon dioxide to flow down on the face and to be absorbed into the faces skin (for example, Patent Document 1). Further, there has been disclosed an instrument of attaching a closable container to specific parts of the human living body, and introducing carbon dioxide thereinto for taking a carbon dioxide bath (for example, Patent Document 2).

CITATION LIST

Patent Documents

Patent Document 1: Japanese Patent Application Publication No. 2008-012268
Patent Document 2: Japanese Patent Application Publication No. 07-171189
Patent Document 3: Domestic Re-publication WO2004/002393

SUMMARY OF INVENTION

Problems to be Solved by the Invention

However, in the cosmetic instrument described in the above Patent Document 1, since it repeats feeding hot water of carbon acid held in the container from its lower part to the upper part by a pump, and causing its flowing-down owing to gravity, carbon dioxide contained in hot water runs away in a short period of time, and this technique has been involved with such a problem that the amount of carbon dioxide absorbed through the skin from the face has been a small quantity.

Further, the devices for taking the carbon dioxide bath described in Patent Documents 2 and 3 can cause carbon dioxide to be effectively and directly absorbed into the skin or mucous membrane in the closed container. But, there has been searched for such a device which enables a more efficient skin-pass absorption of carbon dioxide, oxygen, or a mixed gas of carbon dioxide and oxygen.

In view of the above mentioned problems, it is an object of the invention to provide a gas mist pressure bath device which is possible to realize an effective skin-pass absorption of carbon dioxide, oxygen, or a mixed gas of carbon dioxide and oxygen into the skin or the mucous membrane of the head of the living-body by contacting thereto at pressure higher than a predetermined value.

Means for Solving the Problem

Therefore, the present invention is to provide a gas mist pressure bath device, which causes oxygen, carbon dioxide or a mixed gas (called as "gas" hereafter) of oxygen and carbon dioxide at density higher than a predetermined value to contact the skin or mucous membrane of the head of the living body, composed of a gas mist generation means of generating and supplying a mist (called as "gas mist" hereafter) prepared by pulverizing and dissolving the above mentioned gas and liquid; a compressed air supply means of supplying compressed air; and a living body mask member having a first sealed layer which is shaped to cover the head of the living body and is connected to the gas mist generation means and to the compressed air supply means for sealing the gas mist supplied from the gas mist generation means, and having a second sealed layer for sealing compressed air supplied from the compressed air supply means, characterized by causing the gas mist within the first sealed layer to contact the skin or mucous membrane of the head of the living body by the second sealed layer at pressure higher than a predetermined value.

Otherwise, the present invention is to provide the gas mist pressure bath device, which causes oxygen, carbon dioxide, or the mixed gas (called as "gas" hereafter) of oxygen and carbon dioxide at density higher than the predetermined value to contact the skin or mucous membrane of the head of the living body, composed of a gas mist generation means of generating and supplying under pressure a mist (called as "gas mist" hereafter) prepared by pulverizing and dissolving the above mentioned gas and liquid; and a living body mask member which is shaped to cover the head of the living body and is connected to the gas mist generation means and is shaped with a sealing layer for sealing the gas mist supplied under pressure from the gas mist generation means, characterized by causing the gas mist within the sealed layer to contact the skin or mucous membrane of the head of the living body at pressure higher than the predetermined value.

By the way, the invention refers it as "pulverizing and dissolving" to pulverize the liquid into fine liquid drops, and cause to contact and mix with gas (carbon dioxide, or oxygen, or the mixed gas of carbon dioxide and oxygen).

In addition, the head of the living body referred to in this invention generally includes the frontal region, parietal region, occipital region, temporal region, and face.

The living body pressure bath mask should be hood-shaped for covering at least the frontal region, parietal region, occipital region, temporal region and face, or face mask-shaped for covering at least the face of the living body. The living body pressure bath mask should be opened for securing breath of a user. Further, for attaching and detaching the living body pressure bath mask, there is provided a fastening means formed with any one or a combination of a rubber, string or a face fastener, thereby to avoid the gas mist from blowing off into atmosphere.

On the other hand, it is preferable to use the above mentioned liquid with any one or plural combination of water, ionic water, physiological salt solution or liquid containing medicines. The medicines desirably are any of menthol, vitamin E, vitamin C derivative, retinol, anesthetic, cyclodextrin, complex of photocatalyst and apatite, hyaluronic acid, coenzyme Q10, seed oil, propolith, carbonated spring agent of high density, anti-allergic agent, anti-inflammatory agent, antipyretic agent, anti-fungus, carcinostatic agent, anti-arrhythmic agent or anti-influenza viral agent.

Next, the compressed air supply means carries out interval pressurization (pulse pressurization) by compressed air. Or, the gas mist generation device supplies under pressure the gas mist, taking intervals.

The gas mist generation device has a gas introducing portion inserted with a gas bomb sealing gas and a storage for receiving liquid, and generates the gas mist by making air babbles of gas in the gas bomb and releasing them into the storage. Temperature of the liquid within the gas mist generation device is suitably centigrade 40 to 70.

The compressed air supply means has a heater means, and supplies hot air or cool air by turning the heater means ON/OFF. Desirably, air pressure supplied from the compressed air supply means is turned at 1.02 to 2.5 air pressure.

Herein, the compressed air supply means preferably employs (1) compressed air bomb, (2) electro drive compressor, or (3) hand-operated bag-shaped pneumatic compressor (for example, a manual-operated air bag used to a blood pressure meter, or a foot-operated type pneumatic compressor used as an air inflator of a ring buoy).

Pressure of the gas mist supplied into the inside of the living-body mask member from the gas mist generation means is good at 1.02 to 2.5 air pressure.

Sizes of the gas mist supplied from the gas mist generation means into the living-body cover member are suitably smaller than 10 μm.

Desirably, the gas mist generation means has a gas mist supply pipe for supplying the gas mist into the living-body mask member, and this gas mist supply pipe has a filter for removing liquid drops attached to a pipe inside. Further, a whole or one part of the gas mist supply pipe is suitably composed of a cornice shaped pipe, and this gas mist supply pipe is provided with a check valve, and the living-body mask member is also provided with the check valve at a supply port of the gas mist.

Advantageous Effects of Invention

According to the gas mist pressure bath device of the invention, since the gas mist is not merely caused to contact the skin or the mucous membrane of the living body, but contact at pressure being higher than predetermined value, gas absorption efficiency from the skin or the mucous membrane can be considerably heightened comparing with the prior art. In particular, if making a double layer structure of the living body pressure bath mask of covering the head, pressurization is not only made easy, but also it is made unnecessary to heighten pressure of the gas mist itself, and therefore skin-pass absorption can be accelerated without requiring much amount of gas.

DESCRIPTION OF EMBODIMENTS

In the following description, explanations will be made to the embodiments of this invention, referring to the attached drawings.

First Embodiment

Figure 1:
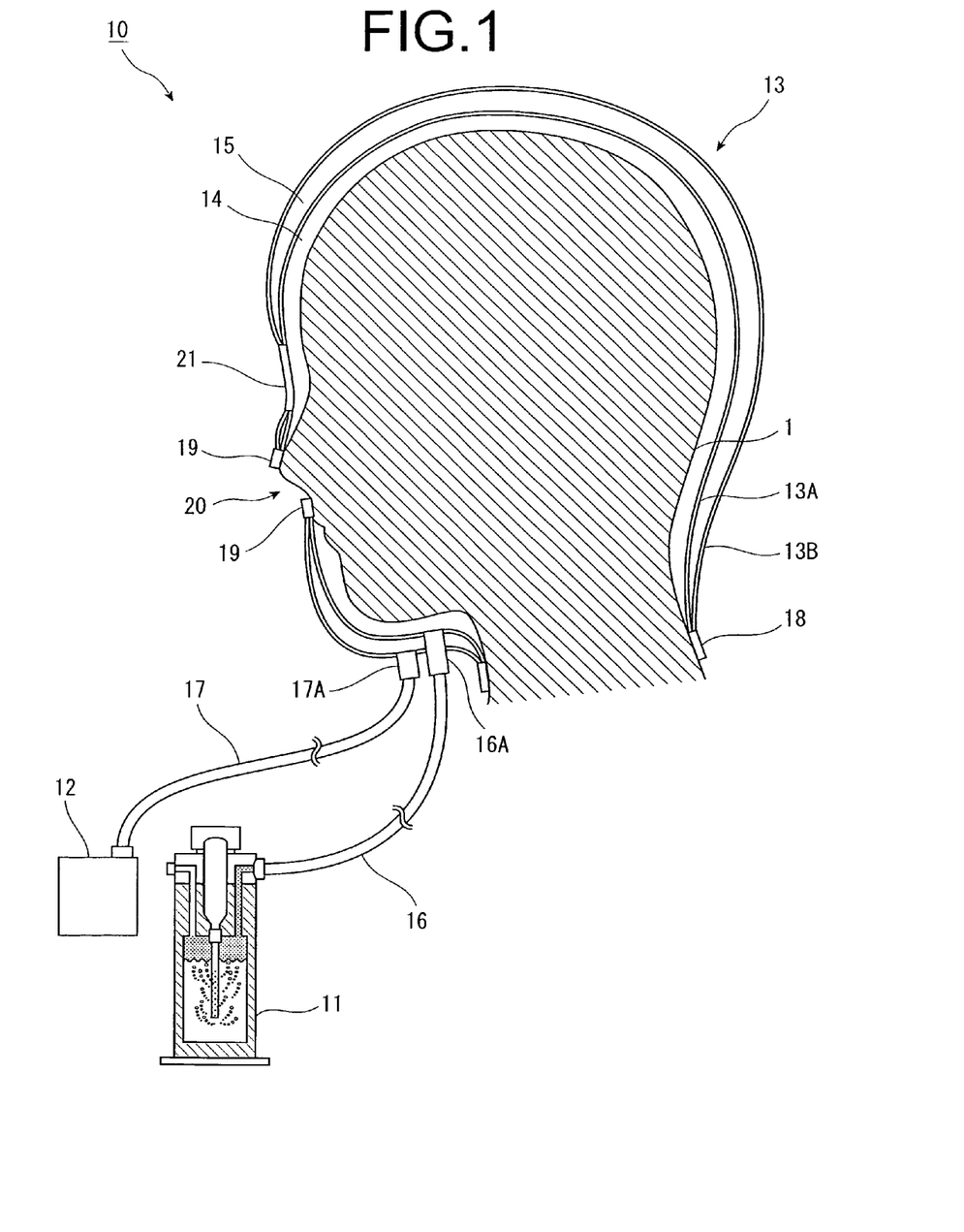
FIG. 1 A cross sectional and typical view of the gas mist pressure bath device depending on a first embodiment of the invention.
Figure 2:
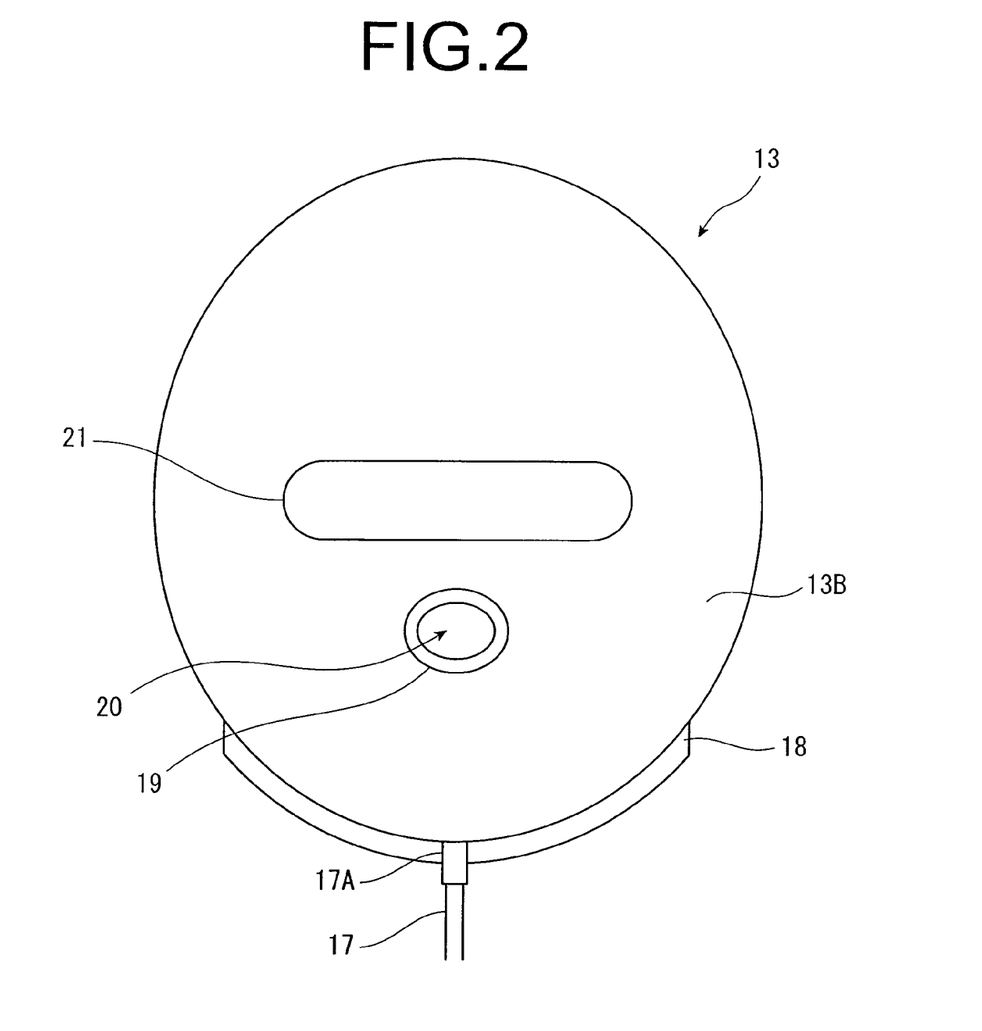
FIG. 2 A front view of the of the gas mist pressure bath device depending on the first embodiment of the invention.
Figure 3:
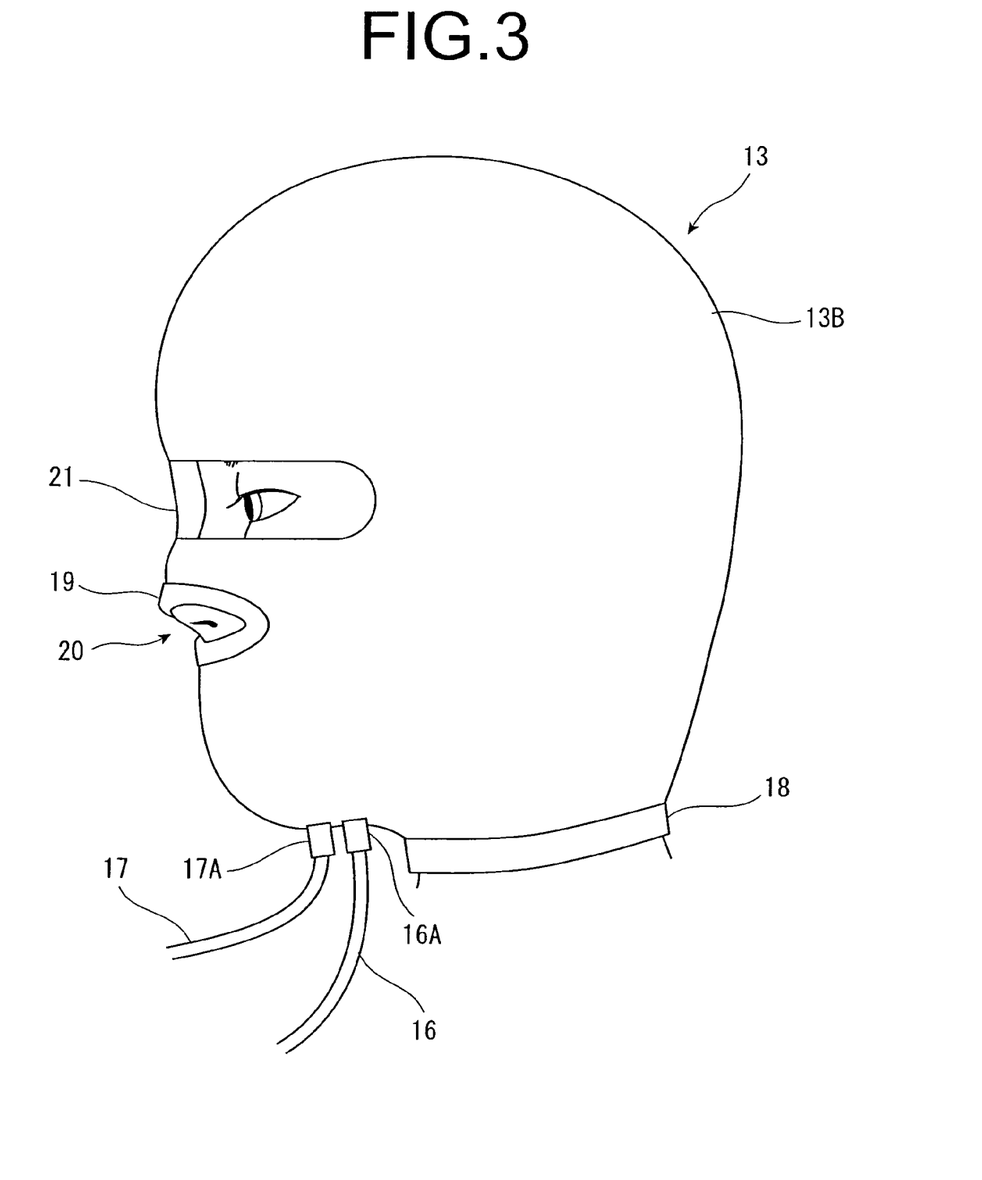
FIG. 3 A typical view showing a condition of actually putting on the living body pressure bath mask of the gas mist pressure bath device depending on the first embodiment of the invention.
Figure 4:
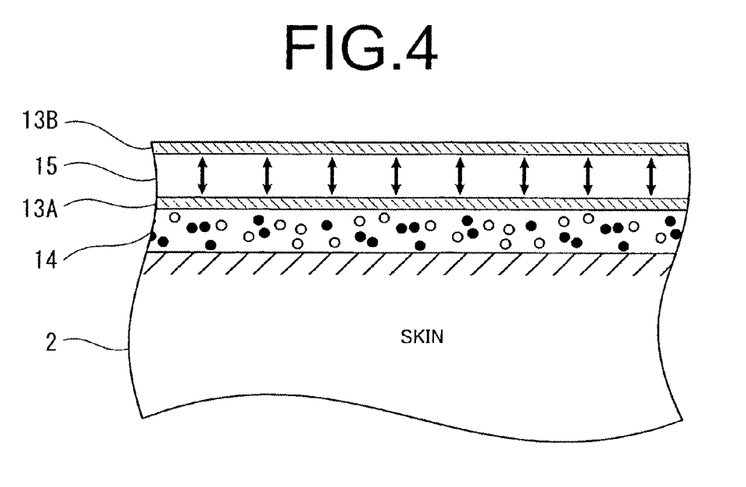
FIG. 4 An enlarged view of a principal part showing the contacting relation between the gas mist and the skin or mucous membrane of the gas mist pressure bath device depending on the first embodiment of the invention.

FIG. 1 is the cross sectional and typical view of the gas mist pressure bath device depending on the first embodiment of the invention, FIG. 2 is the front view of the living body pressure bath mask of the gas mist pressure bath device, FIG. 3 is the typical view showing the condition of actually putting on the living body pressure bath mask thereof, and FIG. 4 is the enlarged view of the principal part showing the contacting relation between the gas (carbon dioxide, oxygen, or a mixed gas of carbon dioxide and oxygen) and the skin or mucous membrane.

The gas mist pressure bath device 10 depending on this embodiment is, as shown in these Figures, composed of the gas mist generation device 11 for generating and supplying the gas mist, the compressor 12 for supplying compressed air, and the living body pressure bath mask (living body mask member) 13 for covering the head of the user 1 (herein, frontal region, parietal region, occipital region, temporal region, and face) and causing the gas mist to contact the skin or mucous membrane (including the scalp) and to be absorbed there.

The living body pressure bath mask 13 is composed of an inside mask 13A and an outside mask 13B, this inside mask 13A filling the gas mist in relation with the skin or mucous membrane of the user 1, and the outside mask 13B filling compressed air in relation with the inside mask 13A to pressurize the gas mist within the inside mask 13A. These inside mask 13A and outside mask 13B are formed with double layers as one body.

The living body pressure bath mask 13 has stoppers 18 at an attaching and detaching opening for preventing leakage of the gas mist and sealing the inside of the mask. The gas mist is supplied into the inside mask 13A from the gas mist generation device 11, while the compressed air is supplied into the outside mask 13B from the compressor 12 via connecting tubes 16, 17, respectively. Thereby, as shown in FIG. 4, there are formed a gas mist layer 14 between the inside mask 13A and the skin or mucous membrane of the user 1, and a pressurized layer 15 of compressed air between the inside mask 13A and the outside mask 13B. The pressurized layer 15 pressurizes the gas mist layer 14 from the outside to the skin or mucous membrane 2 for accelerating absorption of gas from the skin or mucous membrane 2.

The inside mask 13A and the outside mask 13B are made of the woven or non-woven fabric of a non-air permeable and non-moisture permeable material, for example, polyethylene, polypropylene, poly vinylidene, polystylene, polyvinylacetate, polyvinyl chloride, nylon or polytetrafluoroethylene.

The stoppers 18 of the living body pressure bath mask 13 are composed of a material having moderately stretching property for fitting to the user's neck, and stop thereunto to close the inside of the inside mask 13A (gas mist layer 14). Since the inside mask 13A and the outside mask 13B are connected to the stoppers 18, the pressurized layer 15 has a structure having previously sealing property. Herein, the stopper 18 is desirably composed of, e.g., a face fastener having stretching property. Further, on the inside of the stopper 18, a sealing property may be increased by furnishing a material attaching to the skin or mucous membrane of the user 1. Otherwise, the stopper 18 may be single of or combined with string or rubber, or may be structured to stop by tightening of air pressure.

The living body pressure bath mask 13 has an aperture 20 at a position corresponding to a user's nose for his breathing. Around the aperture 20, an adhering portion 19 is furnished for holding the sealing property within the living body pressure bath mask 13. The adhering portion 19 is made of a material adhering to the skin or mucous membrane 2 of the user 1, for example, such as a visco-elastic gel, or may be made to use a double-tape each time when using it. When using, at first, the aperture 20 is placed at the position corresponding to a nostril of the user 1, and the adhering portion 19 is fixed by adhering it around the user's nostril. Thereby, breathing of the user 1 can be secured and the gas mist is prevented from leaking from the aperture 20.

The living body pressure bath mask 13 further has a window 21 for maintaining fields of view of the user 1. The window 21 is made of a material of transparent or semi-transparent non-air and non-moisture permeable substance, and applied to a position corresponding to the user's eyes. By the way, if the using gas is carbon dioxide or the mixed gas of oxygen and carbon dioxide, this structure may have the aperture and the adhering portion, similarly to the case of the nostril.

As shown in FIG. 1, the inside mask 13A has a connector 16A for connecting an end of a connecting tube (gas mist supply pipe) 16 which is connected to the gas mist generation device 11 at its one end. The connector 16A has a check valve at its inside for avoiding back-flow of the gas mist. Also, an outside mask 13B has a connector 17A for connecting an end of a connecting tube 17A connected to a connecting tube 17 connected to the compressor 12 at its one end. The connecting tubes 16, 17 are formed with taps at their ends though not showing, and can be connected to the connectors 16A, 17A in screwing or mounting manners. Further on, the connecting tubes 16, 17 have the check valves at their insides for avoiding the back-flow of the gas mist. Although not showing, the connecting tube 16 has a filter for removing liquid drops attached to the pipe inside.

Figure 9:
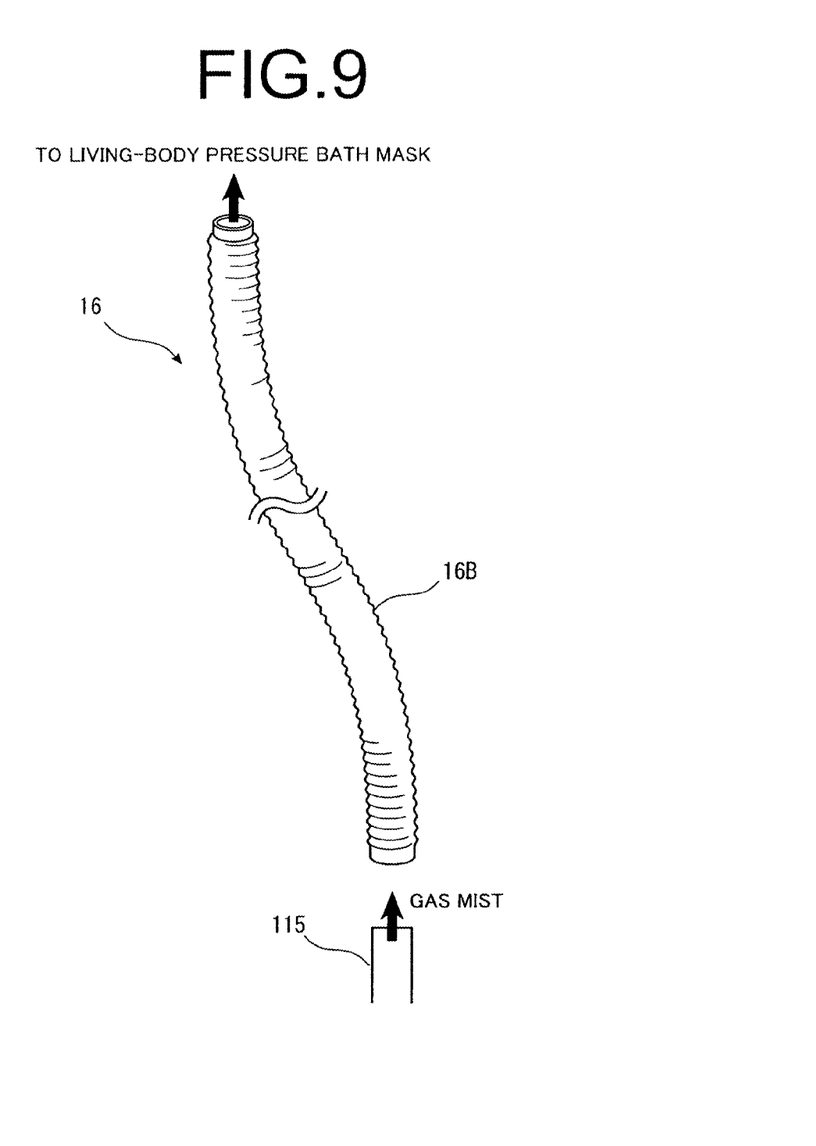
FIG. 9 A typical view showing one example of a connection pipe (gas mist supply pipe) used to the gas mist pressure bath device of the present invention.

Further, as shown in FIG. 9, preferably, the connecting tube 16 is overall or partially composed of a soft cornice shaped pipe 16B of a large diameter. If composing with such a corniced pipe 16B, the connecting tube 16 is freely bent and may be expanded so that the user is not restricted in his action. Even if the gas mist flowing in the connecting tube 16 becomes gradually liquefied, the liquid can be removed through concaves and convexes of the cornice.

Figure 5:
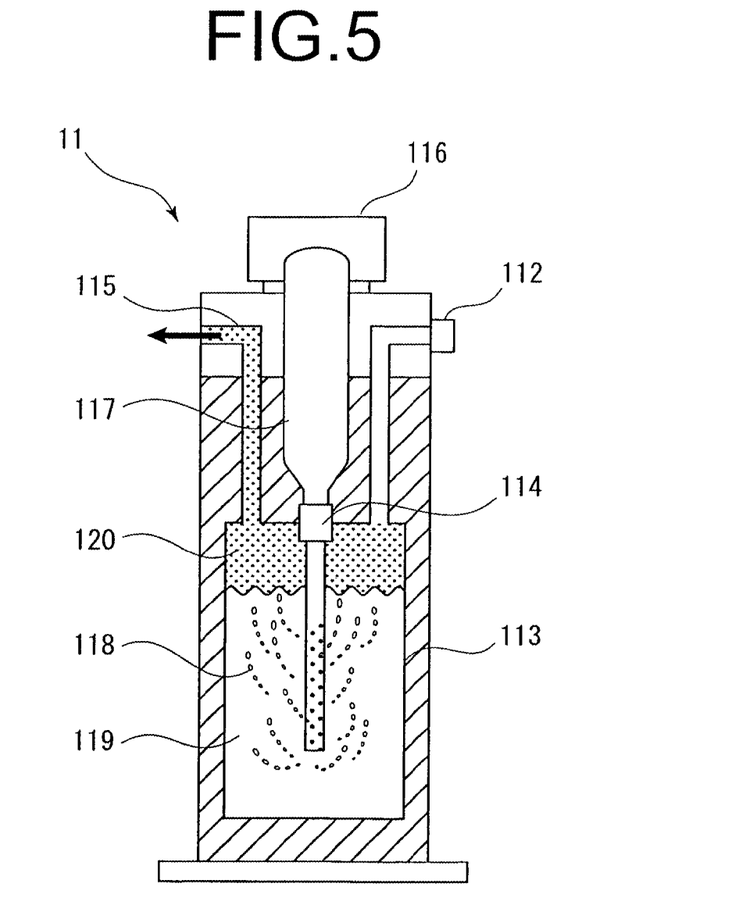
FIG. 5 A typical view of the gas mist generation device of the gas mist pressure bath device depending on the first embodiment of the invention.

As shown in FIG. 5, the gas mist generation device 11 obtains the gas mist by releasing the gas 118 into the liquid 119, and pulverizing and dissolving the liquid 119 and the gas 118. The gas mist generation device 11 is composed of a liquid inlet 112 of pouring the liquid 119, a storage tank 113 of storing the liquid 119 poured from the liquid inlet 112, a gas inserting portion 114 having inside a needle for opening the gas bomb 117 and releasing the gas 118 into the liquid 119 within the storage tank 113, a gas mist supply port 115 for taking out the gas mist 120 generated by releasing the gas 118 into the liquid 119, and a cap 116 of securing the gas bomb 117 and forcing the gas bomb 117 against the gas inserting portion 114.

For obtaining the gas mist 120, at first, the liquid 119 of around centigrade 40 to 70 is poured into the storage tank 113 from the liquid inlet 112. Next, the gas bomb 117 is inserted into the gas inserting portion 114. By tightening the cap 116, the gas bomb 117 is pressed down, and when the cap 116 is perfectly tightened, the gas bomb 117 is opened by the needle provided within the gas inserting portion 114. Then, the gas 118 is dashed into the liquid 119. Thus, the gas mist 120 is generated and is supplied into the inside mask 13A via the connecting tube 16 from the gas mist supply port 115. Sizes of the gas mist then generated are desirably fine, and concretely optimum to be smaller than 10 μm.

Herein, as the liquid 119 poured into the storage tank 113, other than water, ionic water, or physiological salt solution, it is preferable to employ, liquid containing medicines effective to users' diseases or symptoms. For the medicines, there are enumerated, for example, anti-allergic agent, anti-inflammatory agent, anti-febrile, anti-fungus agent, carcinostatic substance, anti-arrhythmic agent, anti-influenza viral agent, and others. Further, these liquids are mixed with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; a complex of photocatalysis having disinfection and anti-phlogistic and apatite; hyaluronic acid having excellent water holding capacity and a skin moisture retention effect; coenzyme Q10 activating cells and heightening immunization; a seed oil containing anti-oxidation substance, or much nutrient; propolith having anti-oxidation function, anti-fungus function, anti-inflammatory function, pain-killing function, anesthetic function, and immunity function, and thus those substances are possible to generate synergistic effects by coupling with a gas physiological action. Further, it is possible to add carbonate spring agent of high density of main components being carbonate and organic acid (as one example of effective components is sulfate, carbonate, organic acid, sodium dichloroisocyanurate).

The structure of the gas mist generation device 11 is not limited to the above mentioned one, but various modifications may be employed. For example, the small sized gas bomb 117 of a cartridge type has now been exemplified, but instead, it is good to connect a gas mist generation device to a large sized gas bomb of operational institute via a valve.

The compressor 12 supplies the compressed air to the pressurized layer 15 of the living body pressure bath mask 13. Air pressure supplied then is determined to be around 1.02 to 2.5 air pressure. Pressurization by the compressed air from the compressor 12 may be always carried out, and effects may be more heightened by predetermined interval in pulse. Pressurization interval at this time increases the effects by synchronizing with stroke of pulse.

As the compressor 12, a compressed air bomb is used. Other than this, for using simply at a house, for example, a domestic bed-cloth dryer or a manual bag shaped compressor (the hand-operated air bag used to the blood pressure meter, or the foot-operated type pneumatic compressor used as the air inflator of the ring buoy) may be used. The compressed air supplied to the compressor 12 may be turned hot.

According to the above mentioned embodiment, since the living body pressure bath mask is the double structure, it is unnecessary to heighten pressure of the gas mist itself, and the skin-pass absorption can be accelerated with a small amount of gas. In addition, the living body pressure bath mask is shaped to cover the whole of the head of the living-body, the gas mist pressure bath can be taken over the wide range of the head.

Second Embodiment

Figure 6:
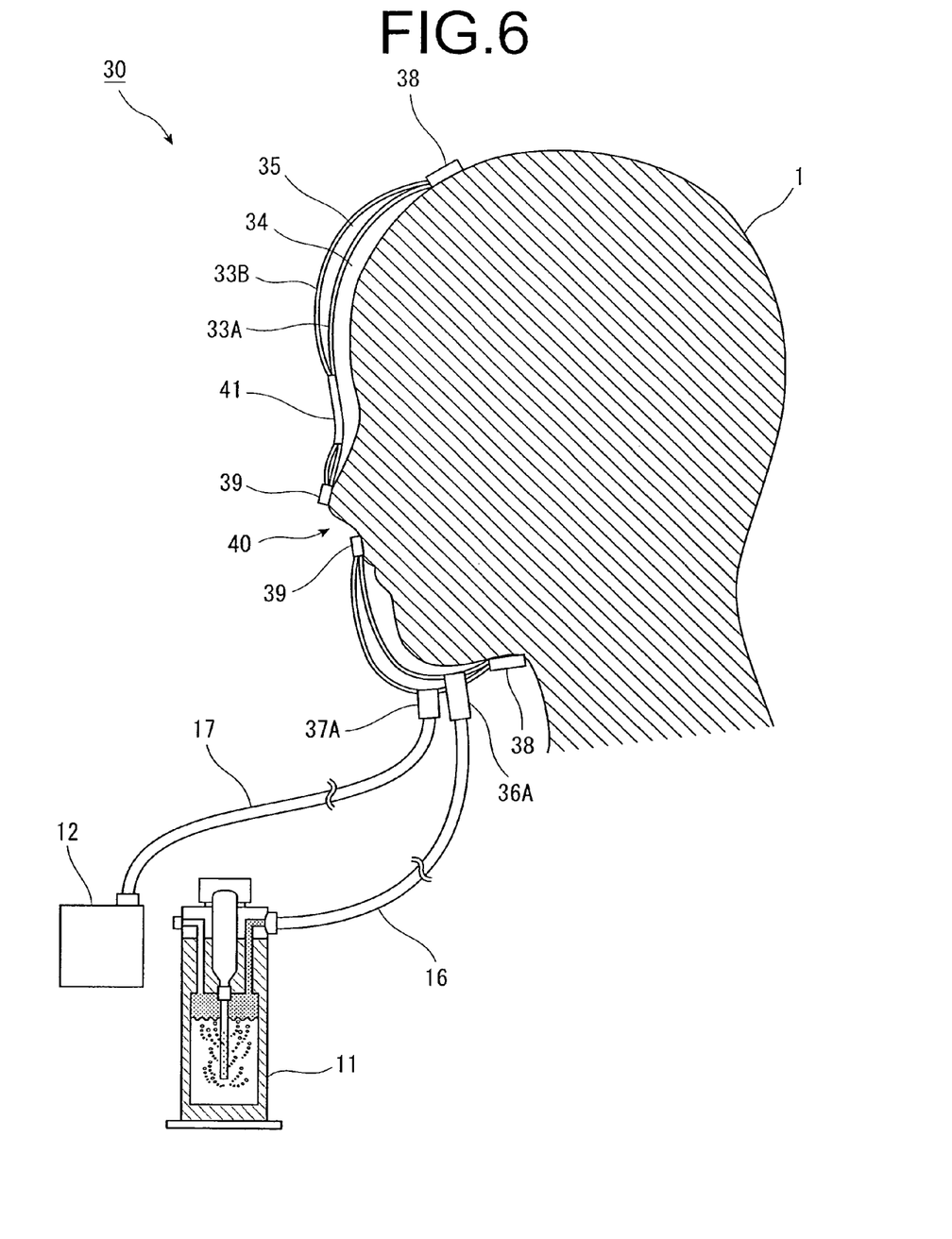
FIG. 6 A cross sectional and typical view of the gas mist pressure bath device depending on a second embodiment of the invention.
Figure 7:
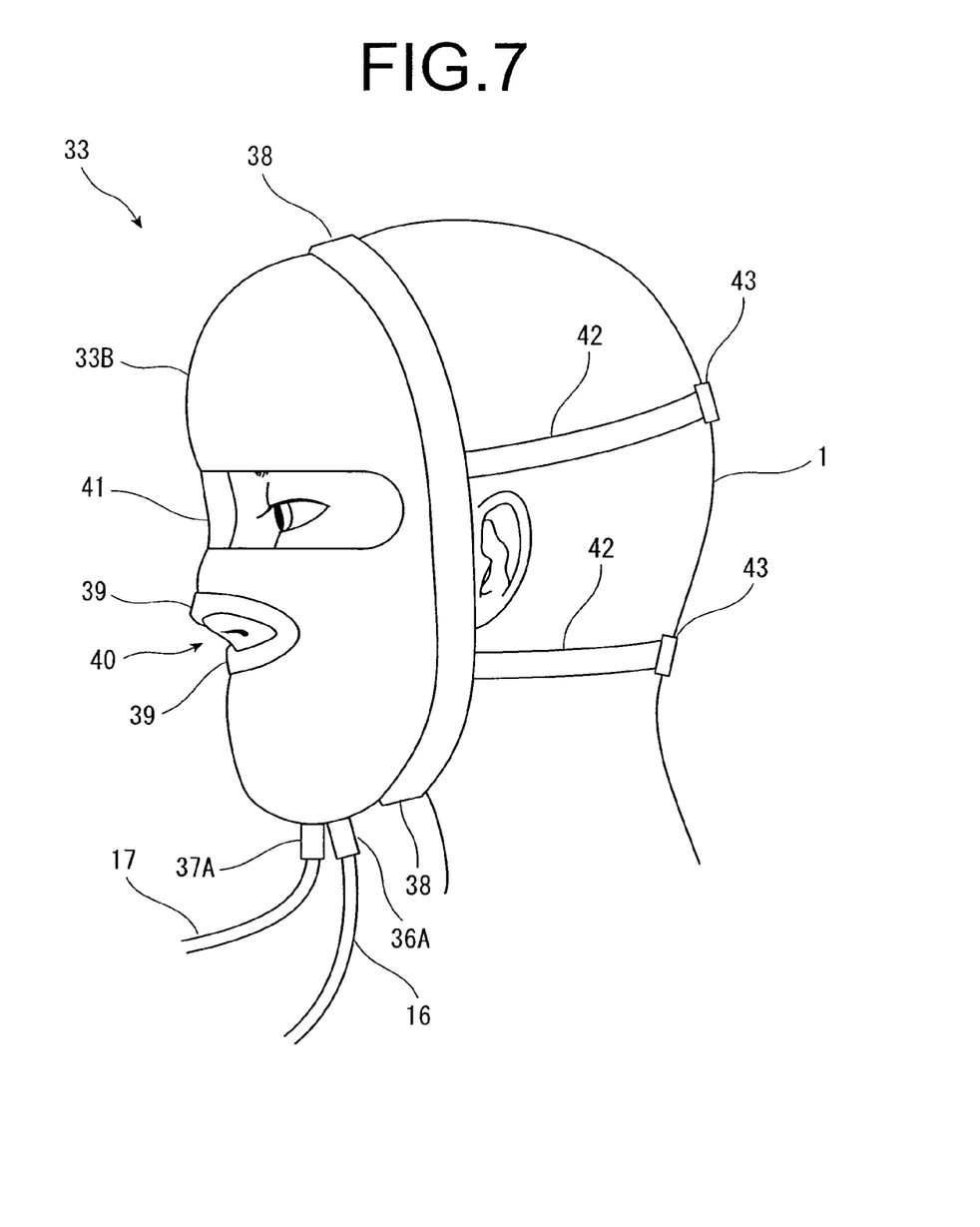
FIG. 7 A typical view showing a condition of actually putting on the living body pressure bath mask of the gas mist pressure bath device depending on the second embodiment of the invention.

FIG. 6 is the cross sectional and typical view of the gas mist pressure bath device depending on the second embodiment of the invention, and FIG. 7 is the typical view showing the condition of actually putting on the living body pressure bath mask thereof. In FIGS. 6 and 7, parts of the same structure as those of FIG. 1 will be given the same numerals, and explanation will be omitted.

Herein, explanation will be mainly made to the gas mist pressure bath device 30 aiming at the gas mist pressure bath for the face only. As shown in FIGS. 6 and 7, the living body pressure bath mask 33 according to the present embodiment has the shape of a face mask for covering the whole of the face, and this is composed of the inside mask 33A and the outside mask 33B. The inside mask 33A and the outside mask 33B are formed as one body, and the gas mist is supplied into the inside mask 33A from the gas mist generation device 11, while the compressed air is supplied into the outside mask 33B from the compressor 12. Thereby, there are formed the gas mist layer 34 between the inside mask 33A and the skin or mucous membrane, and a pressurized layer 35 of the compressed air between the inside mask 33A and the outside mask 33B. The pressurized layer 35 pressurizes the gas mist layer 34 from the outside to the side of the skin for accelerating absorption of the gas mist from the skin or mucous membrane 2.

As shown in FIG. 7, in this embodiment, the living body pressure bath mask 33 is shaped to cover the whole of the user's face, and the living body pressure bath mask 33 has the stopper 38 at its circumference for avoiding leakage of the gas mist. The stopper 38 is composed of a material having moderately stretching property and non-air permeable, non-moisture permeable material for fitting to the circumference of the user's face. The stopper 38 is held at a position for the living body pressure bath mask 33 wrapping the whole face of the user 1, and seals the inside of the inside mask 33A (gas mist layer 34). Since the inside mask 33A and the outside mask 33B are connected to the stopper 38, the pressurized layer 35 has a structure having previously the sealing property. Herein, the stopper 38 is desirably composed of, e.g., the face fastener having the stretching property. Otherwise, the stopper 38 may be single of or combined with string or rubber. In this embodiment, since the stopper 38 has a large diameter, it is necessary to provide a material adhering to the skin or mucous membrane of the user 1, e.g., as the visco-elastic gel on the inside face of the stopper 38 in order to increase in particular the sealing property, or to stop by tightening of air pressure.

Only with the stopper 38 as mentioned above, since the living body pressure bath mask 33 of this embodiment is difficult to securely fix the living body pressure bath mask 33 to the user 1, further stopping belts 42 are prepared. The stopping belt 42 is composed of a material of stretching property, for example, a rubber. The stopping belt 42 is fixed to the living body pressure bath mask 33 at its one end, and is connected to the occipital region of the user 1 at another end (e.g. one touch buckle) for avoiding the living body pressure bath mask 33 from dropping. By the way, other than the rubber belt having belt stoppers 43 as mentioned above, such a structure of knotting strings at appropriate portions may be employed. By putting on a stopping mask having the stretching property (for example, the full face mask having an opening at the positions of the aperture 40 or the window 41 of the living body pressure bath mask 33) over the living body pressure bath mask 33, the living body pressure bath mask 33 may be secured. In sum, any means may be used if being able to prevent the living body pressure bath mask 33 from dropping.

The living body pressure bath mask 33 has an aperture 40 at a position corresponding to the user's nose for his breathing. Around the aperture 40, an adhering portion 39 is furnished for holding a sealing property within the living body pressure bath mask 33. The adhering portion 39 is made of a material adhering to the skin or mucous membrane of the user 1, for example, such as the visco-elastic gel, or may be made to use a double-tape each time when using it. When using, at first, the aperture 40 is placed at the position corresponding to the nostril of the user 1, and the adhering portion 39 is fixed by adhering it around the user's nostril. Thereby, breathing of the user 1 can be secured and the gas mist is prevented from leaking from the aperture 40.

The living body pressure bath mask 33 further has a window 41 for securing the fields of view of the user 1. The window 41 is made of a material of transparent or semi-transparent non-air permeable and non-moisture permeable substance, and applied to a position corresponding to the user's eyes. By the way, if the using gas is carbon dioxide or the mixed gas of oxygen and carbon dioxide, this structure may have the aperture and the adhering portion, similarly to the case of the nostril.

As shown in FIG. 6, the inside mask 33A has a connector 16A for connecting an end of a connecting tube 16 which is connected to the gas mist generation device 11 at its one end. The connector 36A has a check valve at its inside for avoiding back-flow of the gas mist. Also, an outside mask 33B has a connector 37A for connecting an end of a connecting tube 17A connected to a connecting tube 17 connected to the compressor 12 at its one end. The connecting tubes 16, 17 are formed with taps at their ends though not showing, and can be connected to the connectors 36A, 37A in the screwing or mounting manners.

According to the above mentioned embodiment, since the shape of the living body pressure bath mask is made the face mask for covering the face, the gas mist pressure bath can be performed efficiently covering the face.

Third Embodiment

Figure 8:
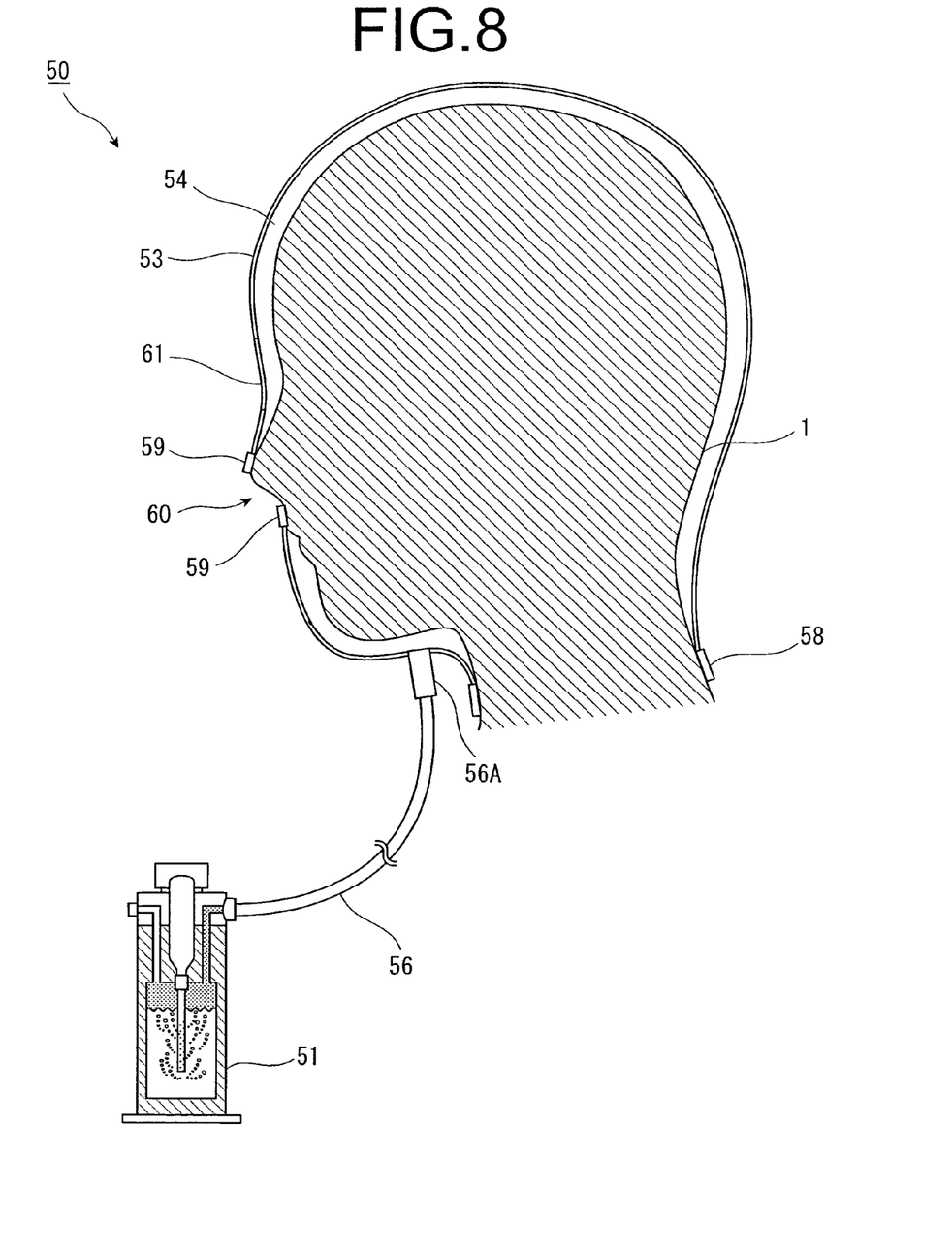
FIG. 8 A cross sectional and typical view of the gas mist pressure bath device depending on a third embodiment of the invention.

FIG. 8 is the cross sectional and typical view of the gas mist pressure bath device depending on the third embodiment of the invention. In FIG. 8, parts of the same structure as those of FIG. 1 will be given the same numerals, and explanation will be omitted.

Herein, explanation will be made to the gas mist pressure bath device 50 having the living body pressure bath mask of forming the gas mist layer only. As shown in FIG. 8, the living body pressure bath mask 53 according to the present embodiment has the shape of covering the head of the user 1 (herein, the frontal region, parietal region, occipital region, temporal region and face). The living body pressure bath mask 53 is supplied inside with the gas mist from the gas mist generation device 51. Thereby, the gas mist layer 54 is formed between the living body pressure bath mask 53 and the skin or mucous membrane. Then, the gas mist is pressurized from the gas mist generation device 51 (pressurized always or in pulse) and introduced to accelerate absorption of the gas mist from the skin or mucous membrane.

The living body pressure bath mask 53 is provided with the stopper 58 at the opening of attaching and detaching to avoid leakage of the gas mist. The stopper 58 is composed of the non-air permeable and non-moisture permeable material having moderately stretching property for fitting to the user's neck, and stop therearound to close the inside of the living body pressure bath mask 53 (gas mist layer 54). Herein, the stopper 58 is desirably composed of, e.g., the face fastener having the stretching property. Further, on the inside of the stopper 58, the sealing property may be increased by furnishing a material attaching to the skin or mucous membrane of the user 1. Otherwise, the stopper 58 may be single of or combined with string or rubber, or may be structured to stop by tightening of air pressure.

The living body pressure bath mask 53 has the aperture 60 at the position corresponding to the user's nose for his breathing. Around the aperture 60, an adhering portion 59 is furnished for holding the sealing property within the living body pressure bath mask 53. The adhering portion 59 is made of the material adhering to the skin or mucous membrane of the user 1, for example, such as a visco-elastic gel, or may be made to use the double-tape each time when using it. When using, at first, the aperture 20 is placed at the position corresponding to the nostril of the user 1, and the adhering portion 59 is fixed by adhering it around the user's nostril. Thereby, breathing of the user 1 can be secured and the gas mist is prevented from leaking from the aperture 60.

The living body pressure bath mask 53 further has the window 61 for securing the fields of view of the user 1. The window 61 is made of the material of transparent or semi-transparent non-air permeable and non-moisture permeable substance, and applied to the position corresponding to the user's eyes. By the way, if the using gas is carbon dioxide or the mixed gas of oxygen and carbon dioxide, this structure may have the aperture and the adhering portion, similarly to the case of the nostril.

As shown in FIG. 8, the living body pressure bath mask 53 has a connector 56A for connecting an end of a connecting tube (gas mist supply pipe) 56 which is connected to the gas mist generation device 51 at its one end. The connector 56A has the check valve at its inside for avoiding back-flow of the gas mist. Although not showing, the connecting tube 56 is formed with the tap at its other end, and can be connected to the connector 56A in the screwing or mounting manners. Further on, the connecting tube 56 has the check valves at the inside for avoiding back-flow of the gas mist. Although not showing, the connecting tube 56 has a filter for removing liquid drops attached to the pipe inside. Also herein, preferably, the connecting tube 56 is whole or partially composed of the cornice shaped pipe of a large diameter.

According to the above mentioned embodiments, since the living body pressure bath mask is formed with one layer, the structure is simplified, and the production cost can be suppressed.

The present invention has been explained in detail, and according to the above gas mist pressure bath device of the invention, since the gas mist is not merely caused to contact the skin or the mucous membrane of the living body, but contact at pressure being higher than predetermined value, the gas absorption efficiency from the skin or the mucous membrane can be considerably heightened comparing with the prior art. In particular, if making the double layer structure of the living body pressure bath mask of covering the head, pressurization is not only made easy, but also it is made unnecessary to heighten pressure of the gas mist itself, and therefore skin-pass absorption can be accelerated without requiring much amount of gas.

The above embodiments have stated concerning the living body pressure bath mask (the first and third embodiments) covering the frontal region, parietal region, occipital region, temporal region and face as the hood, and the living body pressure bath mask (the second embodiment) covering the face only. But the present invention can consider various kinds of living body pressure bath masks such as the living body pressure bath mask of a shape covering the hair as a shower cap, otherwise the living body pressure bath masks as a shape covering parts of the hair (for example, the occipital region only). Those embodiments may be the structure of the two layers in the living body pressure bath mask as the first embodiment, or may be one layer as the second embodiment.

The above embodiments have the aperture at the position corresponding to the user's nose for securing his breathing, but instead, may have the apertures at the position corresponding to the user's mouth (or, both of nose and mouth), and many other modes may be applied which use a breathing tube to be inserted into the nostril or mouth. Furthermore, the window is not necessarily provided for securing the user's field of view. As shown in the first and second embodiments, even if the living body pressure bath mask has the two layered structure, one window may be available, and both of the inside mask and the outside mask are formed with the windows to be the two layers.

The invention is not limited to the above embodiments, and so far as not deviating from the subject matter of the invention, various kinds of embodiments are, of course, available.

INDUSTRIAL APPLICABILITY

The invention relates to the gas mist pressure bath device, in which the gas mist of carbon dioxide, oxygen, or a mixed gas of carbon dioxide, oxygen is directly contacted to the skin or mucous membrane of the living-body for improving a blood circulation, and has an industrial applicability.

REFERENCE SIGNS LIST

1: user
2: skin or mucous membrane
10, 30, 50: gas mist pressure bath device
11, 51: gas mist generation device
12: compressor
13, 33, 53: living body pressure bath mask
13A, 33A: inside mask
13B, 33B: outside mask
14, 34, 54: gas mist layer
15, 35: pressurized layer
16, 17, 56: connecting tube
16A, 17A, 36A, 37A, 56A: connector
16B: cornice shaped pipe
18, 38, 58: stopper
19, 39, 59: connecting portion
20, 40, 60: aperture
21, 41, 61: window
42: stopping belt
43: belt stopper
112: liquid inlet
113: storage tank
114: gas inserting portion
115: gas mist supply port
116: cap
117: gas bomb
118: gas
119: liquid
120: gas mist

The invention claimed is:

1. A gas mist pressure bath device, for contacting a gas including oxygen, carbon dioxide or a mixed gas of oxygen and carbon dioxide at density higher than a predetermined value to a skin or mucous membrane of a head of a living body, comprising:
   a gas mist generation device for generating and supplying a gas mist prepared by pulverizing and dissolving the gas and a liquid;
   a compressed air supply device for supplying compressed air; and
   a living body mask member having a hood-shape to cover a frontal region, a parietal region, an occipital region, a temporal region, and face of the living body and connected to the gas mist generation device and to the compressed air supply device, the living body mask member having
      a first sealed layer for sealing the gas mist supplied from the gas mist generation device,
      a second sealed layer for sealing the compressed air supplied from the compressed air supply device,
      a window portion being made of transparent or semi-transparent and non-air and non-moisture permeable substance, and being placed only at a position corresponding to eyes for securing a field of view,
      an aperture at a position corresponding to a nose of the living body for securing breathing of the living body,
      an adhering portion furnished around the aperture, and adhering to the skin or the mucous membrane of the head of the living body, and the first and the second sealed layers being connected together with the adhering portion,
      an attaching and detaching opening for the mask member, and
      a stopper at the attaching and detaching opening to avoid the gas mist from blowing-off into atmosphere, the stopper being formed of a stretchable material to fit a neck of the living body,
   wherein the gas mist within the first sealed layer is caused to contact the skin or the mucous membrane of the head of the living body by the second sealed layer at a pressure higher than a predetermined value, and the first and the second sealed layer are connected together at a circumferential edge of the window and fixed thereto, and the first and the second sealed layers exist in three sections, between an upper portion of the adhering portion and a lower portion of the circumference edge of the window, between an upper portion of the circumference edge of the window and a part of the stopper, and between a lower portion of the adhering portion and another part of the stopper.

2. A gas mist pressure bath device as set forth in claim 1, wherein the compressed air supply device carries out interval pressurization by compressed air.

3. A gas mist pressure bath device as set forth in claim 1, wherein the gas mist generation device includes a gas bomb sealing the gas, a storage for storing the liquid and a gas inserting portion having a needle thereinside for opening the gas bomb and releasing the gas of the gas bomb into the liquid in the storage, and generates the gas mist by releasing the gas of the gas bomb into the storage.

4. A gas mist pressure bath device as set forth in claim 3, wherein the liquid is centigrade 40 to 70.

5. A gas mist pressure bath device as set forth in claim 1, wherein the compressed air supply device has a heater device, and supplies hot air or cool air by turning the heater device ON/OFF.

6. A gas mist pressure bath device as set forth in claim 1, wherein an air pressure supplied from the compressed air supply device is 1.02 to 2.5 air pressure.

7. A gas mist pressure bath device as set forth in claim 6, wherein the compressed air supply device includes one of a compressed air bomb, an electro drive compressor, and a hand-operated and bag-shaped pneumatic compressor.

8. A gas mist pressure bath device as set forth in claim 1, wherein sizes of the gas mist pressurizingly supplied from the gas mist generation device into the living-body mask member are smaller than 10 μm.

9. A gas mist pressure bath device as set forth in claim 1, wherein the gas mist generation device has a gas mist supply pipe for supplying the gas mist into the living-body mask member, and the gas mist supply pipe has a filter for removing liquid drops attached to an inside thereof.

10. A gas mist pressure bath device as set forth in claim 1, wherein the gas mist generation device has a gas mist supply pipe for supplying the gas mist into the living-body mask member, and at least one part of the gas mist supply pipe is composed of a cornice shaped pipe.

11. A gas mist pressure bath device as set forth in claim 1, wherein the gas mist generation device has a gas mist supply pipe for supplying the gas mist into the living-body mask member, and the gas mist supply pipe is provided with a check valve.

12. A gas mist pressure bath device as set forth in claim 1, wherein the living-body mask member is provided with a check valve at a gas mist supply port.

13. A gas mist pressure bath device as set forth in claim 1, wherein the gas mist generation device has a gas mist supply pipe for supplying the gas mist into the living-body mask member and a connector for connecting the gas mist generation device and the living-body mask member at an end of the gas mist supply pipe, and the connector passes through the second sealed layer and opens to an inside of the first sealed layer.

* * * * *